(12) United States Patent
Ikeda et al.

(10) Patent No.: US 7,790,931 B2
(45) Date of Patent: Sep. 7, 2010

(54) PROCESS FOR PREPARING TETRAFLUOROBENZENE CARBALDEHYDE ALKYL ACETAL

(75) Inventors: Haruhiko Ikeda, Kawasaki (JP); Hideo Miyata, Kawasaki (JP); Katsutoshi Ohno, Kawasaki (JP); Katsuro Urakawa, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 363 days.

(21) Appl. No.: 11/993,302

(22) PCT Filed: Jun. 12, 2006

(86) PCT No.: PCT/JP2006/312187
§ 371 (c)(1),
(2), (4) Date: Dec. 20, 2007

(87) PCT Pub. No.: WO2006/137347
PCT Pub. Date: Dec. 28, 2006

(65) Prior Publication Data
US 2010/0105954 A1   Apr. 29, 2010

Related U.S. Application Data

(60) Provisional application No. 60/695,428, filed on Jul. 1, 2005.

(30) Foreign Application Priority Data

Jun. 22, 2005 (JP) .............................. 2005-181973

(51) Int. Cl.
*C07C 45/42* (2006.01)
*C07C 43/307* (2006.01)
(52) U.S. Cl. ................... 568/436; 568/437; 568/597
(58) Field of Classification Search ............ 568/437, 568/592
See application file for complete search history.

(56) References Cited

U.S. PATENT DOCUMENTS

| 6,624,336 B1 | 9/2003 | Sasaki et al. |
| 7,108,735 B2 | 9/2006 | Hirata et al. |

FOREIGN PATENT DOCUMENTS

| EP | 1 182 184 A1 | 2/2002 |
| JP | 2001-158754 A | 6/2001 |
| KP | 2002-0010907 A | 2/2002 |
| WO | WO 00/68173 A1 | 11/2000 |

OTHER PUBLICATIONS

Shizheng Zhu, et al.: "A new route to 2,3,5,6-tetrafluoroterephthal aldehyde and its chemical transformation", Journal of Fluorine Chemistry, Mar. 1, 2004, vol. 125, Issue 3, pp. 451-454.
Jerry March: "Advanced Organic Chemistry" 1992, John Wiley & Sons, USA, XP002406981, Sections 0-6 and 6-6.

*Primary Examiner*—Sikarl A Witherspoon
(74) *Attorney, Agent, or Firm*—Sughrue Mion, PLLC

(57) ABSTRACT

A process for preparing tetrafluorobenzene carbaldehyde alkyl acetal represented by the following formula (II), comprising reducing tetrafluorocyanobenzene represented by the following formula (I) with a metal catalyst containing a platinum group metal in the presence of an alkyl alcohol represented by R—OH (R is an alkyl group of 1 to 4 carbon atoms) and an acid; (I) wherein m is 1 or 2, n is 0 or 1, and m+n is 2, (II) wherein m and n are the same as those in the formula (I), and R is an alkyl group of 1 to 4 carbon atoms.

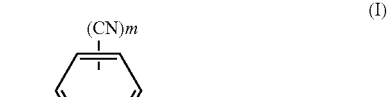

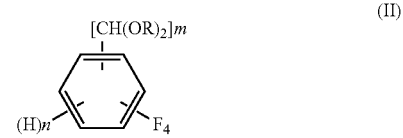

9 Claims, No Drawings

US 7,790,931 B2

PROCESS FOR PREPARING TETRAFLUOROBENZENE CARBALDEHYDE ALKYL ACETAL

CROSS-REFERENCE TO RELATED APPLICATIONS

This application claims the benefit under 35 USC. sctn. 119 of U.S. Provisional Application No. 60/695,428 filed on Jul. 1, 2005.

TECHNICAL FIELD

The present invention relates to a process for preparing tetrafluorobenzene carbaldehyde alkyl acetal which is represented by the following formula (II) and is useful as a raw material, an intermediate or the like for manufacturing agricultural chemicals, medicines, etc.,

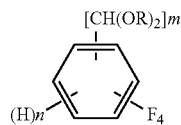
(II)

wherein m is 1 or 2, n is 0 or 1, m+n is 2, and R is an alkyl group of 1 to 4 carbon atoms, and a process for preparing tetrafluorobenzene carbaldehyde, comprising hydrolyzing the acetal to convert it into tetrafluorobenzene carbaldehyde represented by the following formula (III) and then purifying the tetrafluorobenzene carbaldehyde by extraction with a solvent that undergoes two-phase separation between an aqueous phase and a solvent phase,

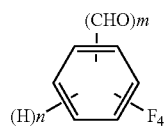
(III)

wherein m and n are the same as those in the formula (II).

More particularly, the invention relates to a process for preparing tetrafluorobenzene carbaldehyde alkyl acetals which are useful as intermediates of cyclopropanecarboxylic acid esters having excellent insecticidal action through the reaction using tetrafluorocyanobenzene as a raw material and a process for preparing tetrafluorobenzene carbaldehyde of high purity by hydrolyzing the acetal obtained by the above process and then purifying the resulting product by a simple and easy method.

BACKGROUND ART

As a process for preparing tetrafluorobenzene carbaldehyde alkyl acetals, there has been heretofore disclosed, for example, a preparation process comprising reducing tetrafluorodicyanobenzene by the use of a sponge nickel catalyst (patent document 1, non-patent document 1). According to these documents, the desired product can be prepared, but sponge nickel that is a catalyst is added into sulfuric acid, so that the catalyst is dissolved and the catalytic amount is increased. Further, the catalyst thus dissolved cannot be used repeatedly. Moreover, there resides a problem that the reaction yield is not so high. As another process for preparing tetrafluorobenzene carbaldehyde, a process comprising performing reduction and hydrolysis of tetrafluorodicyanobenzene using a sponge nickel catalyst in the presence of water (patent document 2) has been disclosed. Also in this process, reaction is carried out in sulfuric acid using sponge nickel as a catalyst, and therefore, the same problem takes place.

Patent document 1: pamphlet of International Publication WO00/68173

Patent document 2: Japanese Patent Laid-Open Publication No. 158754/2001

Non-patent document 1: Journal of Fluorine Chemistry, Vol. 125, pp. 451-454, 2004

DISCLOSURE OF THE INVENTION

Object of the Invention

It is an object of the present invention to provide a process for preparing a tetrafluorobenzene carbaldehyde alkyl acetal compound that is useful as a raw material or an intermediate for manufacturing agricultural chemicals, medicines, etc., and a process for preparing a tetrafluorobenzene carbaldehyde compound, both of said processes being capable of being carried out industrially advantageously.

SUMMARY OF THE INVENTION

The present inventors have earnestly studied, and as a result, they have found that the desired product can be prepared with high purity in a high yield by using tetrafluorocyanobenzene as a raw material and reducing it with a metal catalyst containing a platinum group metal as a catalyst and that the above problem can be solved by this process. Based on the finding, the present invention has been accomplished.

The present invention includes the following matters.

(1) A process for preparing tetrafluorobenzene carbaldehyde alkyl acetal represented by the following formula (II), comprising reducing tetrafluorocyanobenzene represented by the following formula (I) with a metal catalyst containing a platinum group metal in the presence of an alkyl alcohol represented by R—OH (R is an alkyl group of 1 to 4 carbon atoms) and an acid;

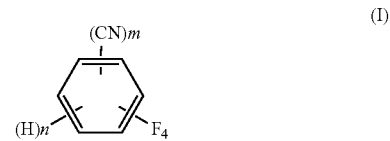
(I)

wherein m is 1 or 2, n is 0 or 1, and m+n is 2,

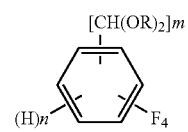
(II)

wherein m and n are the same as those in the formula (I), and R is an alkyl group of 1 to 4 carbon atoms.

(2) The process for preparing tetrafluorobenzene carbaldehyde alkyl acetal as stated in (1), wherein the metal catalyst containing a platinum group metal is used after it is pretreated in a solvent in a hydrogen atmosphere at a temperature of not higher than 100° C.

(3) The process for preparing tetrafluorobenzene carbaldehyde alkyl acetal as stated in (1) or (2), wherein the amount of the acid used is in the range of 1 to 10% by mol based on the amount of a nitrile group of the tetrafluorocyanobenzene.

(4) The process for preparing tetrafluorobenzene carbaldehyde alkyl acetal as stated in any one of (1) to (3), wherein the hydrogen reduction is carried out at a reaction temperature of 30 to 100° C. and a hydrogen partial pressure of atmospheric pressure to 1.5 MPa.

(5) A process for preparing tetrafluorobenzene carbaldehyde, comprising adding water to tetrafluorobenzene carbaldehyde alkyl acetal represented by the following formula (II) to hydrolyze the acetal and thereby convert it into tetrafluorobenzene carbaldehyde represented by the following formula (III) with separating an alkyl alcohol by distillation and then purifying the tetrafluorobenzene carbaldehyde by extraction with a solvent that undergoes two-phase separation between an aqueous phase and a solvent phase;

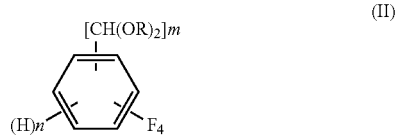

(II)

wherein m is 1 or 2, n is 0 or 1, m+n is 2, and R is an alkyl group of 1 to 4 carbon atoms,

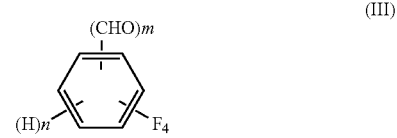

(III)

wherein m and n are the same as those in the formula (II).

EFFECT OF THE INVENTION

In the preparation processes of the invention, a tetrafluorobenzene carbaldehyde alkyl acetal compound and a tetrafluorobenzene carbaldehyde compound can be obtained with high efficiency, and because a by-product is hardly formed, a burden with equipment for further carrying out isolation and purification can be reduced, so that these processes are industrially useful.

BEST MODE FOR CARRYING OUT THE INVENTION

The present invention is described in detail hereinafter.

Examples of the tetrafluorocyanobenzene represented by the formula (I) for use in the preparation process of the invention include tetrafluoromonocyanobenzenes, such as 2,3,4,5-tetrafluorobenzonitrile, 2,3,5,6-tetrafluorobenzonitrile and 2,3,4,6-tetrafluorobenzonitrile, and tetrafluorodicyanobenzenes, such as 3,4,5,6-tetrafluoroorthophthalonitrile, 2,4,5,6-tetrafluoroisophthalonitrile and 2,3,5,6-tetrafluoroterephthalonitrile.

Of the above compounds, tetrafluorodicyanobenzenes are preferable, and 2,3,5,6-tetrafluoroterephthalonitrile is more preferable.

Some of the above compounds are on the market and readily available. Further, the compounds can be synthesized from terephthaloyl chloride by a process described in, for example, Journal of Fluorine Chemistry, Vol. 125, pp. 451-454 (published in 2004).

The preparation process of the invention is a process wherein tetrafluorocyanobenzene represented by the formula (I) is subjected to catalytic reduction with a metal catalyst containing a platinum group metal in the presence of an alkyl alcohol and an acid to prepare a tetrafluorobenzene carbaldehyde alkyl acetal compound represented by the formula (II).

As the reaction in the preparation process of the invention, hydrogenolysis reaction is preferably carried out in a solvent and in the presence of a catalyst using hydrogen. As the catalyst, a metal catalyst is employed, and a catalyst containing a platinum group metal is preferably employed. The platinum group metals refer to elements of ruthenium, rhodium, palladium, osmium, iridium and platinum among the elements belonging to Group 8 of the periodic table (Iwanami Rikagaku Jiten, 4th edition, p. 984). The catalyst may be used in the form of a metal as such or in a supported form.

The supported catalyst is a catalyst wherein metal or metal oxide fine particles comprising one or more kinds of metal species are supported in a highly dispersed state on an carrier, such as silica, alumina, silica-alumina, activated carbon or diatomaceous earth, and is specifically a supported ruthenium-based catalyst, a supported rhodium-based catalyst, a supported palladium-based catalyst, a supported osmium-based catalyst, a supported iridium-based catalyst or a supported platinum-based catalyst.

Further, a modified supported catalyst obtained by adding one or more kinds of the above metal species or other metal species to the above supported catalyst is also employable, and examples of such modified supported catalysts include a supported platinum-alumina catalyst and a supported palladium-rhenium-alumina catalyst.

Examples of preferred catalysts are as follows. Examples of preferred supported catalysts include a supported palladium-based catalyst, a supported rhodium-based catalyst and a supported platinum-based catalyst. Of these catalysts, a supported rhodium-based catalyst is particularly preferable.

Next, the catalytic reduction reaction in the invention is described.

The amount of the catalyst added in the reaction is not specifically restricted and varies according to the form of the catalyst, but in general, the catalyst is preferably used in an amount of not less than 0.1% by mass based on the amount of the tetrafluorocyanobenzene of the formula (I). The amount of the catalyst is more preferably in the range of 0.1 to 100% by mass, particularly preferably 0.1 to 30% by mass. If the catalytic amount is less than 0.1% by mass, the reaction does not proceed smoothly, a large amount of the raw material remains, and the conversion ratio is not increased occasionally. If the catalytic amount exceeds 100% by mass, side reaction is liable to proceed, and the nitrile group sometimes undergoes hydrodecyanation reaction or is sometimes converted into an excessively hydrogenated amino group, so that such an amount is undesirable.

In order to enhance activity and selectivity of the catalyst, it is preferable to carry out pretreatment of the catalyst prior to the reduction reaction. The pretreatment of the catalyst can be carried out by heating and stirring the catalyst in a solvent under hydrogen pressure. The hydrogen pressure is not specifically restricted, and the pretreatment of the catalyst can be carried out at a hydrogen pressure of atmospheric pressure or under hydrogen pressure, and is preferably carried out at a hydrogen partial pressure of atmospheric pressure to 1 MPa. The pretreatment of the catalyst is desirably carried out at a temperature of 30 to 100° C., preferably 30 to 80° C. The solvent for use in the pretreatment of the catalyst is not specifically restricted, but preferred examples of the solvents include saturated aliphatic or alicyclic hydrocarbon solvents, aromatic hydrocarbon solvents, alcohol solvents, ether solvents of aliphatic or alicyclic hydrocarbons, and water. Examples of the saturated aliphatic or alicyclic hydrocarbon solvents include n-hexane, n-octane, isooctane and cyclohexane. Examples of the aromatic hydrocarbon solvents include benzene, toluene and xylene. Examples of the alcohol solvents include alcohols of 1 to 4 carbon atoms, such as methanol, ethanol, n-propanol, isopropanol and n-butanol. Examples of the ether solvents of aliphatic or alicyclic hydrocarbons include diethyl ether, diisopropyl ether, methyl-tertiary butyl ether, tetrahydrofuran, dioxane and dioxolane. It is convenient that a solvent to be used in the reduction reaction is used in this pretreatment, and preferred examples of such solvents include methanol, ethanol, n-propanol, isopropanol and n-butanol.

In the catalytic reduction reaction of the invention, a solvent can be used. The solvent is not specifically restricted, but preferred examples include saturated aliphatic or alicyclic hydrocarbon solvents, aromatic hydrocarbon solvents, alcohol solvents, ether solvents of aliphatic or alicyclic hydrocarbons, and water. Examples of the saturated aliphatic or alicyclic hydrocarbon solvents include n-hexane, n-octane, isooctane and cyclohexane. Examples of the aromatic hydrocarbon solvents include benzene, toluene and xylene. Examples of the alcohol solvents include alcohols of 1 to 4 carbon atoms, such as methanol, ethanol, n-propanol, isopropanol and n-butanol. Examples of the ether solvents of aliphatic or alicyclic hydrocarbons include diethyl ether, diisopropyl ether, methyl-tertiary butyl ether, tetrahydrofuran, dioxane and dioxolane.

The above solvents can be used singly or as a mixed solvent of two or more kinds. When they are used as a mixed solvent, they may be in a state such that they are not homogeneously mixed. Preferred examples of the single solvents include toluene, methanol and dioxane, and preferred examples of the mixed solvents include toluene-methanol, toluene-water, toluene-methanol-water, and dioxane-water. The amount of the solvent used is usually in the range of 0.5 to 30 times by mass, preferably 1 to 20 times by mass, as much as the tetrafluorocyanobenzene. If the amount of the solvent is less than 0.5 time by mass, a problem sometimes occurs in the removal of heat. On the other hand, if the amount thereof exceeds 30 times by mass, the solvent needs to be distilled off when the desired product is isolated, and therefore, too much solvent is undesirable.

The alkyl alcohol represented by the formula R—OH (in this formula, R is an alkyl group of 1 to 4 carbon atoms), which is used in the invention, is an alkyl alcohol of 1 to 4 carbon atoms. Specifically, methanol, ethanol, n-propanol, isopropanol, n-butanol or the like is employed. In order to promote acetalation reaction, methanol having small steric hindrance is most preferable. The alcohol is used in quantities of not less than twice the molar quantity of the nitrile group of the tetrafluorocyanobenzene represented by the formula (I), and is desirably used in quantities of not less than 10 times the molar quantity of the nitrile group.

In the present invention, an acid is necessary. Examples of the acids used in the invention include sulfuric acid, hydrochloric acid, phosphoric acid, formic acid, acetic acid, monochloroacetic acid, dichloroacetic acid and trifluoroacetic acid. Of these, sulfuric acid is particularly preferably employable. The quantity of the acid used is desirably in the range of 1 to 10 times the molar quantity of the nitrile group of the tetrafluorocyanobenzene of the formula (I). If the quantity of the acid is less than 1 time the molar quantity of the nitrile group, an imine form produced in the progress of the reaction is not stabilized, and the reaction does not smoothly proceed occasionally. If the quantity of the acid exceeds 10 times the molar quantity of the nitrile group, the catalyst is sometimes deactivated by the acid, so that such quantity is undesirable.

The catalytic reduction of the invention can be carried out by heating the reaction system to a given temperature after hydrogen is introduced into a gas phase zone or by introducing hydrogen after a gas phase zone is purged with an inert gas and the reaction system is heated to a given temperature. The method to introduce hydrogen is not specifically restricted, and hydrogen may be blown into the reaction solution, may be passed through the gas phase zone or may be fed to the gas phase zone intermittently. The hydrogen gas for use in the reaction does not necessarily have to be a high-purity one and may contain an inert gas or the like exerting no particular influence on the hydrogenation reaction. The reaction is usually carried out at a temperature of 30 to 100° C., preferably 30 to 90° C., more preferably 50 to 80° C. If the temperature is low, formation of an amine as a by-product and denitrilation reaction proceed because of excessive hydrogenation, and the yield of a desired product is sometimes lowered. In contrast, if the reaction temperature is high, the catalyst is deactivated by the acid, and the hydrogen absorption rate is lowered. As a result, the yield of a desired product is sometimes lowered. In the present invention, the hydrogen partial pressure at the reaction temperature is not specifically restricted provided that the reaction proceeds, but in order to inhibit formation of an amine as a by-product and denitrilation reaction caused by excessive hydrogenation, the hydrogen partial pressure is desirably low. The hydrogen partial pressure is preferably in the range of atmospheric pressure to 1.5 MPa, more preferably atmospheric pressure to 0.9 MPa, particularly preferably atmospheric pressure to 0.5 MPa.

The mode of the reaction is not specifically restricted, and a catalytic suspension flow process, a fixed bed flow process, a trickle bed process, a batch process of the like is adoptable.

The tetrafluorobenzene carbaldehyde alkyl acetal of the formula (II) formed by the reduction reaction of the invention can be isolated and purified by solvent distillation, extraction, recrystallization or the like after the catalyst is separated by filtration.

By hydrolyzing the tetrafluorobenzene carbaldehyde alkyl acetal of the formula (II) in the presence of water and the acid, it can be converted into tetrafluorobenzene carbaldehyde represented by the formula (III). The quantity of water is not specifically restricted, but water in quantities of not less than twice the molar quantity of the nitrile group of the tetrafluorocyanobenzene of the formula (I) is necessary. In order to smoothly promote the reaction, an excess quantity of water can be used without any trouble.

By performing so-called reaction distillation for distilling off an alcohol contained in the raw material and an alcohol formed by the reaction to shift the equilibrium to the product side in the hydrolysis reaction, it becomes possible to efficiently convert the contained tetrafluorobenzene carbaldehyde alkyl acetal of the formula (II) into tetrafluorobenzene carbaldehyde represented by the formula (III). According to the reaction distillation, the equilibrium can be efficiently shifted to the product side, and therefore, it becomes possible to greatly decrease the amounts of the acid and water used in the hydrolysis reaction.

Although the tetrafluorobenzene carbaldehyde represented by the formula (III) which is obtained by the hydrolysis reaction can be purified by means of distillation, extraction, two-phase separation or the like, extraction with an organic solvent is preferable because it is simple and easy. The solvent used for the extraction is not specifically restricted provided that it undergoes two-phase separation between an aqueous phase and a solvent phase, and examples of such solvents include saturated aliphatic or alicyclic hydrocarbon solvents, aromatic hydrocarbon solvents, ether solvents of aliphatic or alicyclic hydrocarbons, and saturated aliphatic halogen solvents. Of these, aromatic hydrocarbons such as toluene are preferably employed.

EXAMPLES

The present invention is further described with reference to the following examples, but it should be construed that the invention is in no way limited to those examples.

An analytical instrument and analytical conditions used in the examples are as follows.

Gas chromatography analysis (referred to as "GC analysis" hereinafter)

Analytical instrument: HP6850 manufactured by HP

Column: DB-1 manufactured by J & W, 30 m×0.32 mm×1 μm

Column temperature: 80° C., raised up to 200° C. at 5° C./min, raised up to 290° C. at 15° C./min, held for 11 minutes Integrator: HP 3396

Injection temperature: 300° C.

Detector temperature: 300° C.

Flow rate: constant pressure 7.91 psi (68.5 ml/min, 80° C.)

Split ratio: 50

Detector: FID, $H_2$ 30 ml/min, Air 300 ml/min

Carrier gas: He

Gas chromatography quantitative analysis (referred to as "GC quantitative analysis" hereinafter)

Internal standard: 1,2-dichlorobenzene

Example 1

In a conical flask, 20.6 g of 95% sulfuric acid was slowly added dropwise to 70 g (2.2 mol) of methanol with ice cooling. Then, into a 300-ml glass autoclave, the resulting sulfuric acid/methanol solution and a 5% Rh/C catalyst (available from NE Chemcat Corporation, hydrous product) in an amount of 0.25 g on a dry weight basis were charged. The system was purged with hydrogen to make a hydrogen pressure 0.1 MPa at room temperature. Heating of the autoclave and stirring of the contents in the autoclave were started, and the temperature was increased to 40° C. and was held constant for 1 hour. After the autoclave was cooled, 10 g (50 mmol) of tetrafluoroterephthalonitrile (available from Tokyo Kasei Kogyo Co., Ltd.) was fed to the autoclave, and the temperature was raised to 70° C. in a nitrogen atmosphere. At 70° C., introduction of hydrogen was started. The reaction pressure was controlled so that the hydrogen absorption rate should become not more than 10 ml/min. After a lapse of 6 hours and 30 minutes, absorption of hydrogen ceased. The quantity of hydrogen absorbed was 119% of the theoretical quantity of hydrogen absorbed. The reaction solution was filtered to separate the catalyst, and methanol was distilled off at atmospheric pressure. Thereafter, 100 g of water was added to the residue, and the mixture was refluxed by heating at an internal temperature of 100° C. for 60 minutes. Then, methanol formed by hydrolysis of acetal was distilled off at atmospheric pressure. When the top temperature of the distillation reached 99° C., the distillation was finished, and the resulting solution was cooled to room temperature. Then, the solution was extracted 3 times each with 30 g of toluene.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 92.0 mol %, the amount of 2,3,5,6-tetrafluorobenzene was 0.94 mol %, and the amount of 2,3,5,6-tetrafluorobenzonitrile was 0.79 mol %. On the other hand, the aqueous phase was neutralized and then subjected to GC analysis. As a result of the analysis, presence of 3.39 mol % of 2,3,5,6-tetrafluorobenzylamine was confirmed. The results are set forth in Table 1.

Comparative Example 8

The same operations as in Example 1 were carried out, except that as a catalyst a 5% Pd/C catalyst (available from NE Chemcat Corporation, hydrous product) was charged in an amount of 0.25 g on a dry weight basis. After a lapse of 3.3 hours, absorption of hydrogen ceased. The quantity of hydrogen absorbed was 117% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, and the amount of tetrafluoroterephthalaldehyde was 68.9 mol %. On the other hand, the aqueous phase was neutralized and then subjected to GC analysis. As a result of the analysis, presence of 14.8 mol % of 2,3,5,6-tetrafluorobenzylamine was confirmed. The results are set forth in Table 1.

Example 3

The same operations as in Example 1 were carried out, except that the temperature of the pretreatment of the catalyst with hydrogen was changed from 40° C. to 50° C. After a lapse of 5.5 hours, absorption of hydrogen ceased. The quantity of hydrogen absorbed was 106% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 89.4 mol %, the amount of 2,3,5,6-tetrafluorobenzene was 1.31 mol %, and the amount of 2,3,5,6-tetrafluorobenzonitrile was 1.03 mol %. On the other hand, the aqueous phase was neutralized and then subjected to GC analysis. As a result of the analysis, presence of 2.35 mol % of 2,3,5,6-tetrafluorobenzylamine was confirmed. The results are set forth in Table 1.

Example 4

The same Operations as in Example 1 were carried out, except that the reaction temperature was changed from 70° C. to 80° C. After a lapse of 5.5 hours, absorption of hydrogen ceased. The quantity of hydrogen absorbed was 99% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 87.5 mol %, the amount of 2,3,5,6-tetrafluorobenzene was 2.00 mol %, and the amount of 2,3,5,6-tetrafluorobenzonitrile was 1.61 mol %. On the other hand, the aqueous phase was neutralized and then subjected to GC analysis. As a result of the analysis, presence of 2.16 mol % of 2,3,5,6-tetrafluorobenzylamine was confirmed. The results are set forth in Table 1.

Example 5

The same operations as in Example 1 were carried out, except that the amount of sulfuric acid used was changed from 20.6 g to 12.9 g (125 mmol). After a lapse of 7.0 hours, absorption of hydrogen ceased. The quantity of hydrogen absorbed was 73% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 84.5 mol %, the amount of 2,3,5,6-tetrafluorobenzene was 1.00 mol %, and the amount of 2,3,5,6-tetrafluorobenzonitrile was 0.83 mol %. On the other hand, the aqueous phase was neutralized and then subjected to GC analysis. As a result of the analysis, presence of 4.14 mol % of 2,3,5,6-tetrafluorobenzylamine was confirmed. The results are set forth in Table 1.

Example 6

The same operations as in Example 1 were carried out, except that the amount of tetrafluoroterephthalonitrile was changed from 10 g to 20 g (100 mmol). After a lapse of 8.3 hours, absorption of hydrogen ceased. The quantity of hydrogen absorbed was 76% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 89.6 mol %, the amount of 2,3,5,6-tetrafluorobenzene was 0.63 mol %, and the amount of 2,3,5,6-tetrafluorobenzonitrile was 0.54 mol %. On the other hand, the aqueous phase was neutralized and then subjected to GC analysis. As a result of the analysis, presence of 2.98 mol % of 2,3,5,6-tetrafluorobenzylamine was confirmed. The results are set forth in Table 1.

Example 7

The same operations as in Example 1 were carried out, except that the catalyst used was changed from the 5% Rh/C catalyst (available from NE Chemcat Corporation, hydrous product) to a 2% Rh/C catalyst (available from NE Chemcat Corporation, hydrous product). After a lapse of 7.3 hours, absorption of hydrogen ceased. The quantity of hydrogen absorbed was 114% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 88.6 mol %, the amount of 2,3,5,6-tetrafluorobenzene was 1.15 mol %, and the amount of 2,3,5,6-tetrafluorobenzonitrile was 2.63 mol %. On the other hand, the aqueous phase was neutralized and then subjected to GC analysis. As a result of the analysis, presence of 2.36 mol % of 2,3,5,6-tetrafluorobenzylamine was confirmed. The results are set forth in Table 1.

Example 8

The same operations as in Example 1 were carried out, except that after completion of the reaction the catalyst was recovered by filtration and the recovered catalyst was used again. After a lapse of 10.3 hours, absorption of hydrogen ceased. The quantity of hydrogen absorbed was 91% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 80.5 mol %, the amount of 2,3,5,6-tetrafluorobenzene was 1.15 mol %, and the amount of 2,3,5,6-tetrafluorobenzonitrile was below the detection limit. On the other hand, the aqueous phase was neutralized and then subjected to GC analysis. As a result of the analysis, presence of 2.88 mol % of 2,3,5,6-tetrafluorobenzylamine was confirmed. The results are set forth in Table 1.

Comparative Example 1

The same operations as in Example 1 were carried out, except that the amount of the catalyst used was changed from 0.25 g to 0.05 g on a dry weight basis. After a lapse of 7.0 hours, absorption of hydrogen ceased. The quantity of hydrogen absorbed was 83% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, the tetrafluoroterephthalonitrile as a raw material remained in an amount of 21.0 mol %, and tetrafluoroterephthalaldehyde was obtained in an amount of only 5.0 mol %. The amount of 2,3,5,6-tetrafluorobenzene was 0.65 mol %, the amount of 2,3,5,6-tetrafluorobenzonitrile was 0.53 mol %, and 1-cyano-2,3,5,6-tetrafluorobenzaldehyde wherein a nitrile group on only one side had reacted was obtained in an amount of 63.1 mol %. On the other hand, the aqueous phase was neutralized and then subjected to GC analysis. As a result of the analysis, presence of 2.88 mol % of 2,3,5,6-tetrafluorobenzylamine was confirmed. The results are set forth in Table 2.

Comparative Example 2

The same operations as in Example 1 were carried out, except that the catalyst was used without subjecting it to pretreatment with hydrogen. After a lapse of 7.5 hours, absorption of hydrogen ceased. The quantity of hydrogen absorbed was 124% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 81.7 mol %, the amount of 2,3,5,6-tetrafluorobenzene was 1.37 mol %, and the amount of 2,3,5,6-tetrafluorobenzonitrile was 1.09 mol %. On the other hand, the aqueous phase was neutralized and then subjected to GC analysis. As a result of the analysis, presence of 7.29 mol % of 2,3,5,6-tetrafluorobenzylamine was confirmed. The results are set forth in Table 2.

Comparative Example 3

The same operations as in Example 1 were carried out, except that the amount of sulfuric acid used was changed from 20.6 g to 5.15 g (50 mmol). After a lapse of 4.2 hours, absorption of hydrogen ceased. The quantity of hydrogen absorbed was 47% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, and tetrafluoroterephthalaldehyde was obtained in an amount of only 14.5 mol %. The amount of 2,3,5,6-tetrafluorobenzene was 0.81 mol %, the amount of 2,3,5,6-tetrafluorobenzonitrile was 0.67 mol %, and 1-cyano-2,3,5,6-tetrafluorobenzaldehyde wherein a nitrile group on only one side had reacted was obtained in an amount of 54.0 mol %. On the other hand, the aqueous phase was neutralized and then subjected to GC analysis. As a result of the analysis, presence of 0.04 mol % of 2,3,5,6-tetrafluorobenzylamine was confirmed. The results are set forth in Table 2.

Comparative Example 4

The same operations as in Example 1 were carried out, except that the reaction temperature was changed from 70° C. to 120° C. After a lapse of 8.0 hours, absorption of hydrogen ceased. The quantity of hydrogen absorbed was 103% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, and tetrafluoroterephthalaldehyde was obtained in an amount of only 2.6 mol %. The amount of 2,3,5,6-tetrafluorobenzene was 1.08 mol %, the amount of 2,3,5,6-tetrafluorobenzonitrile was 0.87 mol %, and 1-cyano-2,3,5,6-tetrafluorobenzaldehyde wherein a nitrile group on only one side had reacted was obtained in an amount of 42.2 mol %. On the other hand, the aqueous phase was neutralized and then subjected to GC analysis. As a result of the analysis, the amount of 2,3,5,6-tetrafluorobenzylamine was below the detection limit. The results are set forth in Table 2.

Comparative Example 5

The same operations as in Example 1 were carried out, except that the reaction temperature was changed from 70° C. to 20° C. After a lapse of 7.0 hours, absorption of hydrogen ceased. The quantity of hydrogen absorbed was 124% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, and tetrafluoroterephthalaldehyde was obtained in an amount of only 42.2 mol %. The amount of 2,3,5,6-tetrafluorobenzene was 1.75 mol %, and the amount of 2,3,5,6-tetrafluorobenzonitrile was 1.40 mol %. On the other hand, the aqueous phase was neutralized and then subjected to GC analysis. As a result of the analysis, presence of 28.1 mol % of 2,3,5,6-tetrafluorobenzylamine was confirmed. The results are set forth in Table 2.

Comparative Example 6

The same operations as in Example 1 were carried out, except using a catalyst which had been obtained by adding a sponge nickel catalyst (R-239, available from Nikko Rica Corporation) and 3 g of copper sulfate to the sulfuric acid/methanol solution and thereby coating the sponge nickel with copper. After a lapse of 7.9 hours, absorption of hydrogen ceased. The quantity of hydrogen absorbed was 74% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, and tetrafluoroterephthalaldehyde was obtained in an amount of 67.0 mol %. The catalyst was reused in reaction, but the reaction did not proceed. The results are set forth in Table 2.

Comparative Example 7

The same operations as in Comparative Example 6 were carried out, except that the reaction temperature was changed from 70° C. to 20° C. and the amount of copper sulfate added was changed from 3 g to 2 g. After a lapse of 9.3 hours, absorption of hydrogen ceased. The quantity of hydrogen absorbed was 85% of the theoretical quantity of hydrogen absorbed. Treatment of the reaction solution was carried out in the same manner as in Example 1.

From the toluene extract, a small amount of a sample was withdrawn, and it was subjected to GC analysis. As a result of the analysis, a peak of the tetrafluoroterephthalonitrile as a raw material was below the detection limit, the amount of tetrafluoroterephthalaldehyde was 23.9 mol %, and 1-cyano-2,3,5,6-tetrafluorobenzaldehyde wherein a nitrile group on only one side had reacted was obtained in an amount of 16.5 mol %. The catalyst was reused in reaction, but the reaction did not proceed. The results are set forth in Table 2.

TABLE 1

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Reaction conditions | | | | | | | | |
| Methanol | 2200 mmol | 2200 mmol | 2200 mmol | 2200 mmol | 2200 mmol | 2200 mmol | 2200 mmol | 2200 mmol |
| Sulfuric acid | 200 mmol | 200 mmol | 200 mmol | 200 mmol | 125 mmol | 200 mmol | 200 mmol | 200 mmol |
| Catalyst | 5% Rh/C | 5% Pd/C | 5% Rh/C | 5% Rh/C | 5% Rh/C | 5% Rh/C | 2% Rh/C | 5% Rh/C |
| Catalytic amount | 0.25 g | 0.25 g | 0.25 g | 0.25 g | 0.25 g | 0.25 g | 0.25 g | 0.25 g |
| Pretreatment | 40° C., 1 hr | 40° C., 1 hr | 50° C., 1 hr | 40° C., 1 hr | 40° C., 1 hr | 40° C., 1 hr | 40° C., 1 hr | 40° C., 1 hr |
| TFTPN | 50 mmol | 50 mmol | 50 mmol | 50 mmol | 50 mmol | 100 mmol | 50 mmol | 50 mmol |
| Reaction temperature | 70° C. | 70° C. | 70° C. | 80° C. | 70° C. | 70° C. | 70° C. | 70° C. |
| Results | | | | | | | | |
| Reaction time | 6.5 hrs | 3.3 hrs | 5.5 hrs | 5.5 hrs | 7.0 hrs | 8.3 hrs | 7.3 hrs | 10.3 hrs |
| Quantity of hydrogen absorbed | 119% | 117% | 106% | 99% | 73% | 76% | 114% | 91% |
| TFPAD | 92.0% | 68.9% | 89.4% | 87.5% | 84.5% | 89.6% | 88.6% | 80.5% |
| TFB | 0.94% | | 1.31% | 2.00% | 1.00% | 0.63% | 1.15% | n.d. |
| TFBN | 0.79% | | 1.03% | 1.61% | 0.83% | 0.54% | 2.63% | n.d. |
| TFBA | 3.39% | 14.80% | 2.35% | 2.16% | 4.14% | 2.98% | 2.36% | n.d. |

TFPAD: tetrafluoroterephthalaldehyde
TFB: 2,3,5,6-tetrafluorobenzene
TFBN: 2,3,5,6-tetrafluorobenzonitrile
TFBA: 2,3,5,6-tetrafluorobenzylamine

TABLE 2

| | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|
| Reaction conditions | | | | | | | |
| Methanol | 2200 mmol | 2200 mmol | 2200 mmol | 2200 mmol | 2200 mmol | 2200 mmol | 2200 mmol |
| Sulfuric acid | 200 mmol | 200 mmol | 50 mmol | 200 mmol | 200 mmol | 200 mmol | 200 mmol |
| Catalyst | 5% Rh/C | 5% Rh/C | 5% Rh/C | 5% Rh/C | 5% Rh/C | s-Ni (Cu coating) | s-Ni (Cu coating) |
| Catalytic amount | 0.05 g | 0.25 g | 0.25 g | 0.25 g | 0.25 g | Ni: 2 g, copper sulfate: 3 g | Ni: 2 g, copper sulfate: 2 g |
| Pretreatment | 40° C., 1 hr | none | 40° C., 1 hr | 40° C., 1 hr | 40° C., 1 hr | none | none |
| TFTPN | 50 mmol | 50 mmol | 50 mmol | 50 mmol | 50 mmol | 50 mmol | 50 mmol |
| Reaction temperature | 70° C. | 70° C. | 70° C. | 120° C. | 20° C. | 70° C. | 20° C. |
| Results | | | | | | | |
| Reaction time | 7.0 hrs | 7.5 hrs | 4.2 hrs | 8.0 hrs | 7.0 hrs | 7.9 hrs | 9.3 hrs |
| Quantity of hydrogen absorbed | 83% | 124% | 47% | 103% | 124% | 74% | 85% |
| TFPAD | 5.0% | 81.7% | 14.5% | 2.6% | 42.2% | 67.0% | 23.9% |
| TFB | 0.65% | 1.37% | 0.81% | 1.08% | 1.75% | n.d. | n.d. |
| TFBN | 0.53% | 1.09% | 0.67% | 0.87% | 1.40% | n.d. | n.d. |
| TFBA | 0.22% | 7.29% | 0.04% | n.d. | 28.1% | n.d. | n.d. |
| CTFBA | 63.1% | | 54.0% | 42.2% | | | 16.5% |

TFPAD: tetrafluoroterephthalaldehyde
TFB: 2,3,5,6-tetrafluorobenzene
TFBN: 2,3,5,6-tetrafluorobenzonitrile
TFBA: 2,3,5,6-tetrafluorobenzylamine
CTFBA: 1-cyano-2,3,5,6-tetrafluorobenzaldehyde

The invention claimed is:

1. A process for preparing tetrafluorobenzene carbaldehyde alkyl acetal represented by the following formula (II), comprising reducing tetrafluorocyanobenzene represented by the following formula (I) with a catalyst containing rhodium in the presence of an alkyl alcohol represented by R—OH (R is an alkyl group of 1 to 4 carbon atoms) and an acid;

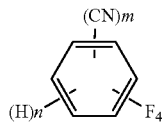

wherein m is 1 or 2, n is 0 or 1, and m+n is 2,

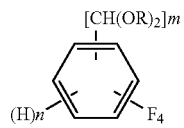

wherein m and n are the same as those in the formula (I), and R is an alkyl group of 1 to 4 carbon atoms.

2. The process for preparing tetrafluorobenzene carbaldehyde alkyl acetal according to claim 1, wherein the catalyst containing rhodium is used after it is pretreated in a solvent in a hydrogen atmosphere at a temperature of not higher than 100° C.

3. The process for preparing tetrafluorobenzene carbaldehyde alkyl acetal according to claim 1, wherein the amount of the acid used is in the range of 1 to 10% by mol based on the amount of a nitrile group of the tetrafluorocyanobenzene.

4. The process for preparing tetrafluorobenzene carbaldehyde alkyl acetal according to claim 1, wherein the hydrogen reduction is carried out at a reaction temperature of 30 to 100° C. and a hydrogen partial pressure of atmospheric pressure to 1.5 MPa.

5. A process for preparing tetrafluorobenzene carbaldehyde, comprising
   (1) preparing tetrafluorobenzene carbaldehyde alkyl acetal represented by the following formula (II) by the process according to any one of claims 1 to 4;
   (2) adding water to the tetrafluorobenzene carbaldehyde alkyl acetal represented by the following formula (II) to hydrolyze the acetal and thereby convert it into tetrafluorobenzene carbaldehyde represented by the following formula (III) while separating the alkyl alcohol by distillation and then purifying the tetrafluorobenzene carbaldehyde by extraction with a solvent that undergoes two-phase separation between an aqueous phase and a solvent phase;

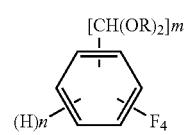

wherein m is 1 or 2, n is 0 or 1, m+n is 2, and R is an alkyl group of 1 to 4 carbon atoms,

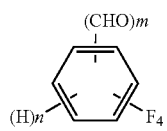

wherein m and n are the same as those in the formula (II).

6. The process for preparing tetrafluorobenzene carbaldehyde alkyl acetal according to claim 2, wherein the amount of the acid used is in the range of 1 to 10% by mol based on the amount of a nitrile group of the tetrafluorocyanobenzene.

7. The process for preparing tetrafluorobenzene carbaldehyde alkyl acetal according to claim 2, wherein the hydrogen reduction is carried out at a reaction temperature of 30 to 100° C. and a hydrogen partial pressure of atmospheric pressure to 1.5 MPa.

8. The process for preparing tetrafluorobenzene carbaldehyde alkyl acetal according to claim 3, wherein the hydrogen reduction is carried out at a reaction temperature of 30 to 100° C. and a hydrogen partial pressure of atmospheric pressure to 1.5 MPa.

9. The process for preparing tetrafluorobenzene carbaldehyde alkyl acetal according to claim 6, wherein the hydrogen reduction is carried out at a reaction temperature of 30 to 100° C. and a hydrogen partial pressure of atmospheric pressure to 1.5 MPa.

* * * * *